(12) United States Patent
Shreve et al.

(10) Patent No.: US 10,302,102 B2
(45) Date of Patent: May 28, 2019

(54) SEAL ASSEMBLIES FOR RECIPROCATING AND ROTARY APPLICATIONS

(71) Applicant: Waters Technologies Corporation, Milford, MA (US)

(72) Inventors: Joshua A. Shreve, Franklin, MA (US); Neal B. Almeida, Cumberland, RI (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 288 days.

(21) Appl. No.: 15/280,421

(22) Filed: Sep. 29, 2016

(65) Prior Publication Data

US 2017/0016461 A1 Jan. 19, 2017

Related U.S. Application Data

(63) Continuation of application No. 13/985,957, filed as application No. PCT/US2012/028414 on Mar. 9, 2012, now Pat. No. 9,488,277.

(Continued)

(51) Int. Cl.
*F15B 15/14* (2006.01)
*F16J 15/3208* (2016.01)
(Continued)

(52) U.S. Cl.
CPC ........ *F15B 15/1461* (2013.01); *F04B 1/0448* (2013.01); *F04B 53/00* (2013.01);
(Continued)

(58) Field of Classification Search
CPC ...... F04B 53/00; F04B 1/0448; F04B 53/143; F15B 15/1461; F16J 15/3208; G01N 30/32; G01N 2030/326
See application file for complete search history.

(56) References Cited

U.S. PATENT DOCUMENTS

| 2,162,104 A | 6/1939 | Mosher |
| 3,771,799 A | 11/1973 | Sekulich et al. |

(Continued)

FOREIGN PATENT DOCUMENTS

| CN | 1732348 A | 2/2006 |
| CN | 101289800 A | 10/2008 |

(Continued)

OTHER PUBLICATIONS

International Search Report and Written Opinion in related international patent application No. PCT/US12/28414, dated May 28, 2013; 10 pages.

(Continued)

*Primary Examiner* — Thomas E Lazo
*Assistant Examiner* — Richard C Drake
(74) *Attorney, Agent, or Firm* — Schmeiser, Olsen & Watts LLP

(57) ABSTRACT

Low-pressure and high-pressure reciprocating and rotary applications use seal assemblies to prevent leakage. One embodiment of a seal assembly includes a major annular body having opposing spaced-apart annular lips extending from a heel portion. The major annular body has a bore extending through the heel portion. A first spring is disposed between the lips, biasing the lips apart. A minor annular body extends from one of the lips of the major annular body. The minor annular body has opposing spaced-apart walls that extend from a base region and form a pocket. A second spring is disposed in the pocket between the spaced-apart walls, biasing the walls apart. During actuator operation, pressurized fluid urges one wall of the minor annular body against a pump head surface to produce a face seal and one of the lips of the major annular body against a rod surface to produce a radial seal.

17 Claims, 10 Drawing Sheets

Related U.S. Application Data

(60) Provisional application No. 61/451,229, filed on Mar. 10, 2011.

(51) Int. Cl.

| | | |
|---|---|---|
| *F04B 1/04* | (2006.01) | |
| *F04B 53/14* | (2006.01) | |
| *G01N 30/32* | (2006.01) | |
| *F04B 53/00* | (2006.01) | |

(52) U.S. Cl.
CPC ......... *F04B 53/143* (2013.01); *F16J 15/3208* (2013.01); *G01N 30/32* (2013.01); *G01N 2030/326* (2013.01)

(56) References Cited

U.S. PATENT DOCUMENTS

| | | | |
|---|---|---|---|
| 4,108,447 A | 8/1978 | Scholin | |
| 4,305,593 A | 12/1981 | Smith | |
| 4,313,828 A | 2/1982 | Brownlee | |
| 4,974,821 A | 12/1990 | Balsells | |
| 5,144,882 A * | 9/1992 | Weissgerber | F04B 53/164 277/550 |
| 5,244,215 A | 9/1993 | Cather, Jr. et al. | |
| 5,556,112 A | 9/1996 | Brandt | |
| 5,788,465 A | 8/1998 | Luongo et al. | |
| 5,979,904 A | 11/1999 | Balsells | |
| 6,029,980 A | 2/2000 | Downes | |
| 6,145,845 A | 11/2000 | Tremoulet, Jr. et al. | |
| 6,161,838 A | 12/2000 | Balsells | |
| 6,926,313 B1 | 8/2005 | Renzi | |
| 7,101,477 B1 | 9/2006 | Willis et al. | |
| 7,588,683 B2 | 9/2009 | Willis et al. | |
| 7,640,841 B2 | 1/2010 | An | |
| 7,828,300 B2 | 11/2010 | Munekata | |
| 8,123,229 B2 * | 2/2012 | Eguchi | F16J 15/3236 277/558 |
| 8,240,672 B2 | 8/2012 | Grace et al. | |
| 9,388,890 B2 * | 7/2016 | Garrett | F16H 25/2418 |
| 9,488,277 B2 * | 11/2016 | Shreve | F04B 1/0448 |
| 2004/0100038 A1 | 5/2004 | Proper | |
| 2004/0256811 A1 | 12/2004 | Proper | |
| 2008/0110515 A1 | 5/2008 | Angelosanto et al. | |
| 2008/0272557 A1 | 11/2008 | Foti | |
| 2009/0321356 A1 | 12/2009 | Gerhardt et al. | |
| 2010/0108164 A1 | 5/2010 | Angelosanto et al. | |
| 2010/0145350 A1 | 6/2010 | Bogert | |
| 2010/0258487 A1 | 10/2010 | Zelechonok et al. | |
| 2011/0006486 A1 | 1/2011 | Niknezhad | |
| 2011/0037234 A1 | 2/2011 | Balsells et al. | |

FOREIGN PATENT DOCUMENTS

| | | |
|---|---|---|
| EP | 0890758 | 1/1999 |
| EP | 2233799 A1 | 9/2010 |
| JP | 04-266664 A | 9/1992 |
| JP | 2006507462 A | 3/2006 |
| JP | 2008510935 A | 4/2008 |

OTHER PUBLICATIONS

Bal Seal Engineering Company, Inc., "Reciprocating Seal Catalog DM-6", Catalog, Jul. 2002, 23 pages.

International Preliminary Report on Patentability in related international patent application No. PCT/US12/28414, dated Sep. 19, 2013; 8 pages.

First Office Action in related Chinese patent application No. 201280012550.4, dated Feb. 4, 2015; 29 pages.

Second Office Action in related Chinese Patent Application No. 201280012550.4, dated Dec. 3, 2015; 24 pages.

First Office Action in counterpart Japanese patent application No. 2013-557889, dated Jan. 26, 2016; 4 pages.

Non-Final Office Action in counterpart U.S. Appl. No. 13/985,957, dated Nov. 3, 2015; 26 pages.

Final Office Action in counterpart U.S. Appl. No. 13/985,957, dated Apr. 20, 2016; 13 pages.

Notice of Allowance and Fee(s) Due in counterpart U.S. Appl. No. 13/985,957, dated Jul. 12, 2016; 13 pages.

* cited by examiner

SEAL ASSEMBLIES FOR RECIPROCATING AND ROTARY APPLICATIONS

RELATED APPLICATIONS

This application claims the benefit of and priority to U.S. provisional application No. 61/451,229, filed Mar. 10, 2011, titled "Seal Assemblies for Reciprocating and Rotary Applications," international application no. PCT/US12/28414, filed Mar. 9, 2012, titled "Seal Assemblies for Reciprocating and Rotary Applications," and U.S. nonprovisional application Ser. No. 13/985,957, filed Aug. 16, 2013, titled "Seal Assemblies for Reciprocating and Rotary Applications," the entireties of which are incorporated by reference herein.

FIELD OF THE INVENTION

The invention relates generally to seal assemblies used in pumps. More specifically, the invention relates to high-pressure and low-pressure seals useful for reciprocating and rotary applications.

BACKGROUND

High-pressure seals play an indispensible role in leakage prevention for those applications, such as liquid chromatography, in which a pump moves fluid under pressure. For instance, in liquid chromatography systems, generally, one or more high-pressure pumps take in solvents and deliver a liquid solvent composition to a sample manager, where a sample awaits injection into the mixture. High-performance liquid chromatography (HPLC) systems, in particular, use high pressure, ranging traditionally between 1,000 psi (pounds per square inch) to approximately 6,000 psi, to generate the flow required for liquid chromatography in packed columns. In contrast to HPLC, ultra-performance liquid chromatography (UPLC) systems use columns with smaller particulate matter and high pressures approaching 18,000 psi to deliver a mobile phase.

Typically, in such liquid chromatography applications, the high-pressure seal resides within a gland in the pump head. The outside diameter (OD) of the high-pressure seal provides a seal against a surface of the gland while the inside diameter (ID) of the high-pressure seal provides a seal against the pump's reciprocating plunger. Some conventional seals designed for high pressure applications though have been found to leak at pressures greater than 6,000 psi.

SUMMARY

In one aspect, the invention features a seal assembly comprising a major annular body having opposing spaced-apart annular lips extending from a heel portion. The major annular body has a bore extending through the heel portion. A first spring is disposed between the lips, biasing the lips apart. A minor annular body extends from one end of one of the lips of the major annular body. The minor annular body has opposing spaced-apart walls that extend from a base region and form a pocket. A second spring is disposed in the pocket between the spaced-apart walls, biasing the walls apart.

In another aspect, the invention features an actuator comprising a movable rod, a pump head for receiving the rod, a wash housing abutting the pump head, and a gland in one of the pump head or the wash housing. The wash housing has a hole through which the rod extends into the chamber of the pump head. A seal assembly is disposed in the gland. The seal assembly comprises a major annular body having opposing spaced-apart lips extending from a heel portion. The major annular body has a bore extending through the heel portion. The bore is sized to closely receive the rod. A first spring is disposed between the lips, biasing the lips apart. A minor annular body extends from one end of one of the lips of the major annular body. The minor annular body has opposing spaced-apart walls that extend from a base region and form a pocket. A second spring is disposed in the pocket between the spaced-apart walls, biasing the walls apart.

In still another aspect, the invention features a seal assembly comprising an annular body having a bore extending therethrough. The annular body has an inner lip opposed to and spaced apart from an outer lip. The inner lip has a lip portion. The outer lip has an overhanging lip portion and a notch behind the overhanging lip portion. The spaced apart lips and the overhanging lip portion together define a pocket. A spring is disposed in the pocket at an angle such that a load line of the spring is directed substantially at a pocket-side of the overhanging lip portion of the outer lip and at a pocket-side of the lip portion of the inner lip. The spring biases the overhanging lip portion of the outer lip and the lip portion of the inner lip apart.

In yet another aspect, the invention features an actuator comprising a movable rod, a pump head with a gland and a rod-receiving chamber, and a wash housing abutting the pump head. The wash housing has a hole through which the rod extends into the chamber of the pump head. A seal assembly is disposed in the gland of the pump head. The seal assembly comprises an annular body having a bore extending therethrough for receiving the rod. The annular body has an inner lip opposed to and spaced apart from an outer lip. The inner lip has a lip portion. The outer lip has an overhanging lip portion and a notch behind the overhanging lip portion. The spaced apart lips and the overhanging lip portion together defining a pocket. A spring is disposed in the pocket at an angle such that a load line of the spring is directed substantially at a pocket-side of the overhanging lip portion of the outer lip and a pocket-side of the lip portion of the inner lip. The spring biases an exterior surface of the overhanging lip portion of the outer lip against a surface of the gland of the pump head while simultaneously biasing an exterior surface of the lip portion of the inner lip against a surface of the rod.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Liquid chromatography is an example of a field of applications wherein fluids are pumped at elevated pressures. Conventionally, high performance liquid chromatography (HPLC) employs pressures ranging between approximately 1,000 and 6,000 psi. Pressures for performing ultra performance liquid chromatography (UPLC) may reach 15,000 to 20,000 psi. Preventing leakage within pumps operating at any of these fluidic pressures is important to the accuracy of the chromatographic results.

The various embodiments of seal assemblies described herein derive from the discovery that leakage of pressurized fluid, when such leakage occurs, generally appears to be the result of insufficient contact pressure between the outside diameter (OD) of the seal assembly and gland surfaces (typically in the pump head) with which the OD seals. Although increasing the spring rate in the seal assembly could improve the sealing force of the OD, this increased spring rate could also negatively affect the effectiveness of the seal provided by inside diameter (ID) of the seal assembly, for example, by increasing friction, torque, and seal wear, and thereby reducing seal life.

In brief overview, the seal assemblies described herein generally improve the OD seal without negatively affecting the ID seal. Tests show these seal assemblies prevent leakage at approximately 18,000 psi. Simulations show that these seal assemblies are able to prevent leakage at least as high as 20,000 psi. One embodiment employs a pressure relief feature on the outside diameter of the seal assembly. In comparison to seal assemblies without the relief feature, the contact pressure is lower between the OD and the gland surface at the locus of the relief feature, with a commensurate increase of contact pressure between the OD and the gland surface elsewhere.

Another embodiment of seal assembly forgoes reliance on the OD to provide the seal against the gland surface. This type of seal assembly has an outer lip with a hinged lip portion that produces a face seal. An angled load line of a spring of the seal assembly contributes to the contact pressure of the face seal against the gland surface and to the contact pressure of the radial seal against the plunger surface.

Yet another embodiment of seal assembly decouples the sealing requirements of the OD from those of the ID by employing two separate springs: an ID spring and an OD spring. The ID spring contributes to the sealing of the ID with the plunger or shaft of the actuator and the OD spring contributes to a face seal with a gland surface. Accordingly, the choice of spring rate of the OD spring does not affect the plunger seal life, and the choice of spring rate of ID spring does not affect the face sealing. In addition, the geometry of the face seal minimizes deformation of the OD.

Figure 1:
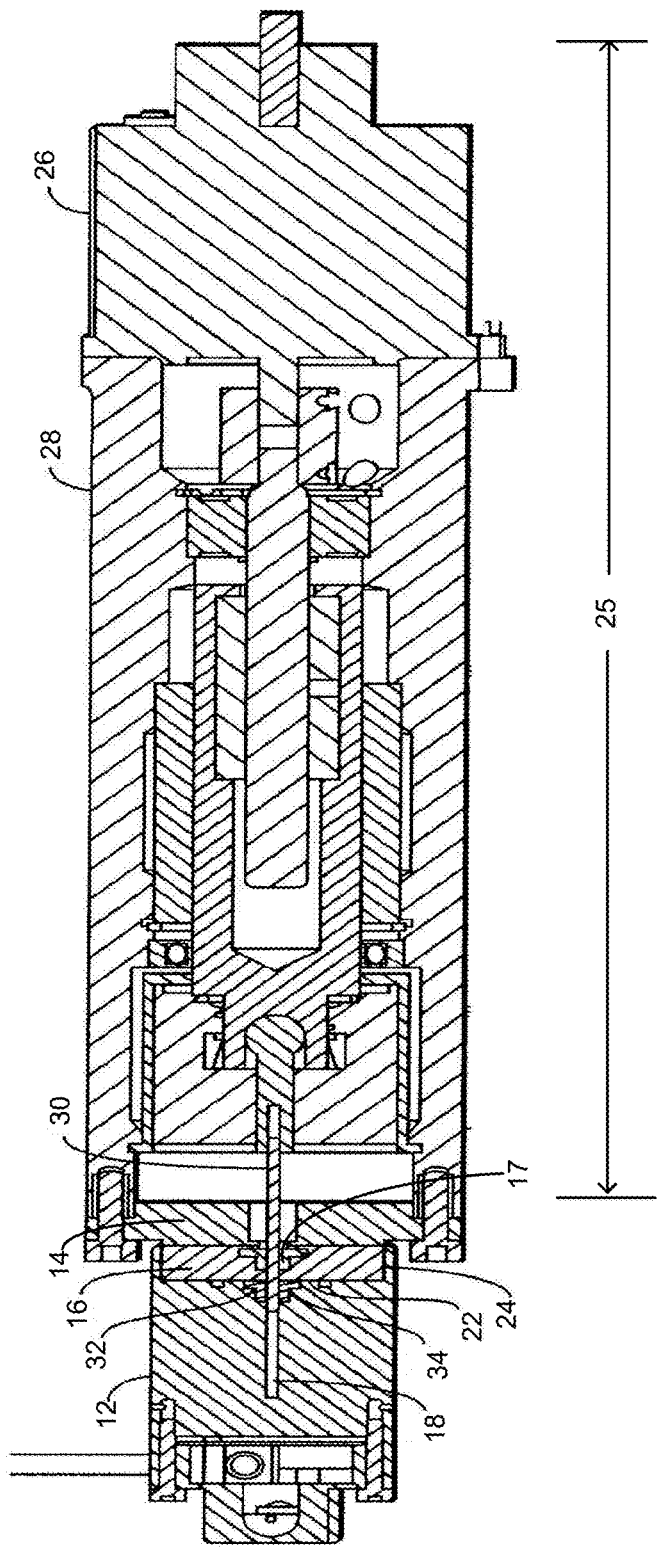
FIG. 1 is a cross-section diagrammatic view of an embodiment of an actuator and seal assembly that can be used in liquid chromatography applications.

FIG. 1 shows an embodiment of an actuator 10 having a pump head 12 and a wash housing 16 affixed to a support plate 14. In one embodiment, the actuator 10 is a part of a binary solvent manager (BSM), which uses two individual serial flow pumps to draw solvents from their reservoirs and deliver a solvent composition. An example implementation of a BSM is the ACQUITY UPLC Binary Solvent Manager, manufactured by Waters Corp. of Milford, Mass.

The pump head 12 includes a chamber 18 and a wash-housing abutment surface 22. The pump head 12 also has a recess 24 for receiving and aligning the wash housing 16. The wash housing 16 provides a chamber 23 (FIG. 2) to collect liquid and wash the plunger of any particulate that may form on the plunger surface. A low-pressure seal assembly, for example, a wash seal 17, is used to contain the liquid in the wash housing 16. The chamber 18 has an inlet (not shown) and an outlet (not shown) for receiving and discharging fluids, respectively. The actuator 10 also includes an actuator body 25 with a motor 26, a drive mechanism 28 mechanically linked to a plunger 30, and an annular plunger seal 32. The plunger 30 extends through the wash seal 17 and the annular plunger seal 32 into the chamber 18 of the pump head 12.

As an example, the plunger seal 32 is retained within a gland 34 of the pump head 12. In other embodiments, the plunger seal 32 is disposed within a gland of the wash housing 16. Contact between a surface of the inside diameter of the plunger seal 32 and the circumference of the plunger 30 produces an ID radial seal. Contact between one or more surfaces of the outside diameter of the plunger seal 32 and a surface of the gland 34 produces an OD seal. During reciprocating actuator operation, the chamber 18 contains fluid under pressure. The plunger 30 moves in and out of the chamber 18, causing the pressurized fluid to move from the inlet to the outlet. Pressurized fluid also pushes against the OD and ID contact surfaces of the plunger seal 32.

The actuator 10 shown in FIG. 1 is only one example of a machine within which the seal assemblies described herein may be used. The features of the actuator 10 (e.g., the pump head 12, gland 34, wash housing 16) may be modified to accommodate different embodiments of the plunger seal 32, as described in more detail below. Although described in connection with reciprocating plungers, the seal assemblies described herein can also be used with rotary shafts, such as a shaft that rotates and turns a rotor fitted to a stator. The term "rod" is used herein to broadly encompass plungers, shafts, rods, and pistons, whether reciprocating or rotary.

Figure 2:
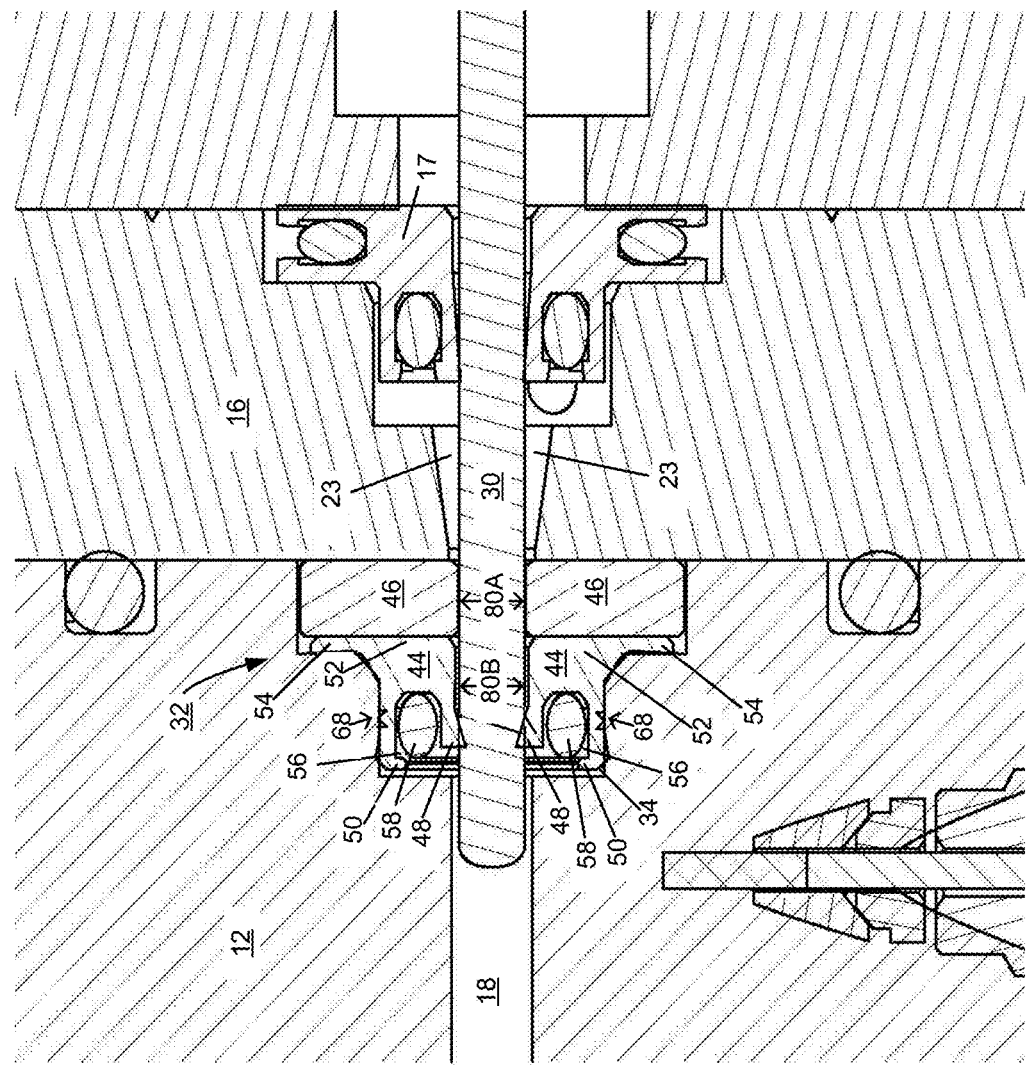
FIG. 2 is a detail view of an embodiment of the seal assembly.

FIG. 2 shows a detail view of an embodiment of the plunger seal 32 of FIG. 1. The pump head 12 is coupled to the wash housing 16. The gland 34 of the pump head 12 retains the plunger seal 32. The plunger seal 32 includes a ring seal 44 and a backup ring 46. The ring seal 44 can be made of a soft plastic; the backup ring 46 can be made of a polyether ether ketone (PEEK). The plunger 30 extends through a bore 80A in the backup ring 46 and a bore 80B in the ring seal 44.

The ring seal 44 has spaced-apart opposing lips 48, 50, respectively, extending generally orthogonally from a heel portion 52. Extending laterally from the heel portion 52 is an extension flange 54. The heel portion 52 and extension flange 54 abut one side of the backup ring 46. The opposing lips 48, 50 and heel portion 52 define a spring pocket 56 within which is disposed a spring 58. Preferably, the spring 58 is of a canted coil type that produces a near constant force across a large displacement range, although other types of springs can be used without departing from the principles described herein. Lip 48, referred to as the inner lip, has a contact surface on its inside diameter that seals against the surface of the reciprocating plunger 30. Lip 50, referred to as the outer lip, has a contact surface on its outside diameter that seals against a surface of the gland 34 in the pump head 12. The outside diameter of the outer lip 50 has a pressure relief feature 68, the shape of which is designed to reduce the contact pressure of the outer diameter against the surface of the gland 34 near the feature, resulting in increasing the contact pressure at other locations of the outer diameter. In this embodiment, the pressure relief feature 68 has a half-bow tie shape with a peak bounded on two sides by parallel grooves.

Figure 3B:
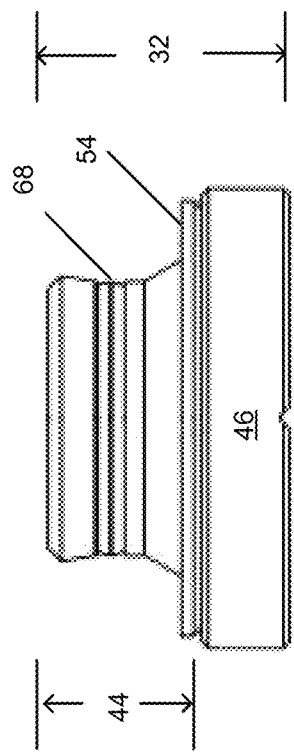
FIG. 3B is a side view of the seal assembly of FIG. 2.
Figure 3D:
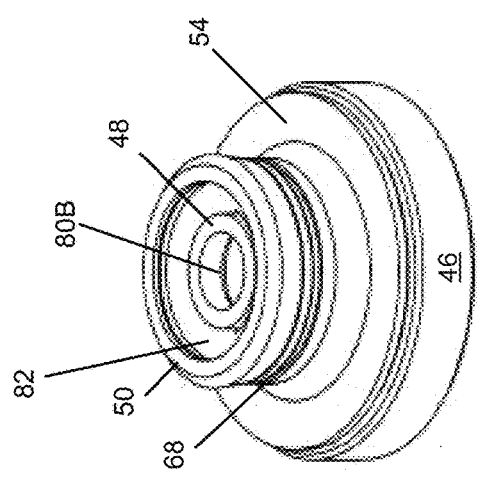
FIG. 3D is an isometric view of the seal assembly in a first orientation.
Figure 3A:
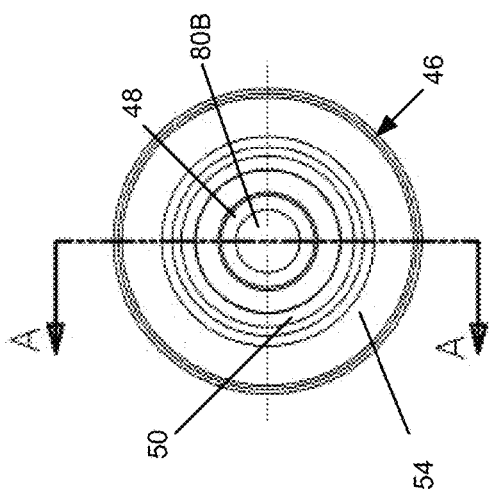
FIG. 3A is an end view of the seal assembly of FIG. 2.

FIGS. 3A-3D show various views of one embodiment of the plunger seal 32. FIG. 3A shows the end of the plunger seal 32 that enters first and is press fit into the gland 34 of the pump head 12. The plunger seal 32 includes the bore 80B through the ring seal 44, inner lip 48, outer lip 50, extension flange 54, backup ring 46 and a spring cavity 82. The spring cavity 82 extends into the spring pocket 56 (FIG. 2). Cross-section line AA passes through the center of the plunger seal 32.

FIG. 3B shows a side view of the plunger seal 32, including the circumferential pressure relief feature 68 formed in the outside diameter of the outer lip 50. In one embodiment, the diameter of the backup ring 46 is approximately 0.3425 inches, and the diameter of the extension flange 54 is approximately 0.324 inches.

Figure 3C:
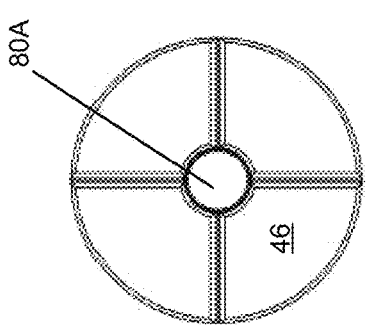
FIG. 3C is another end view of the seal assembly of FIG. 2.

FIG. 3C shows an end view of the plunger seal 32 from the end having the backup ring 46. The bore 80A extends centrally through the backup ring 46. FIG. 3D shows an isometric view of the plunger seal 32, with the backup ring 46 at the bottom of the figure. The bore 80B extends through the ring seal 44 (FIG. 2).

Figure 3E:
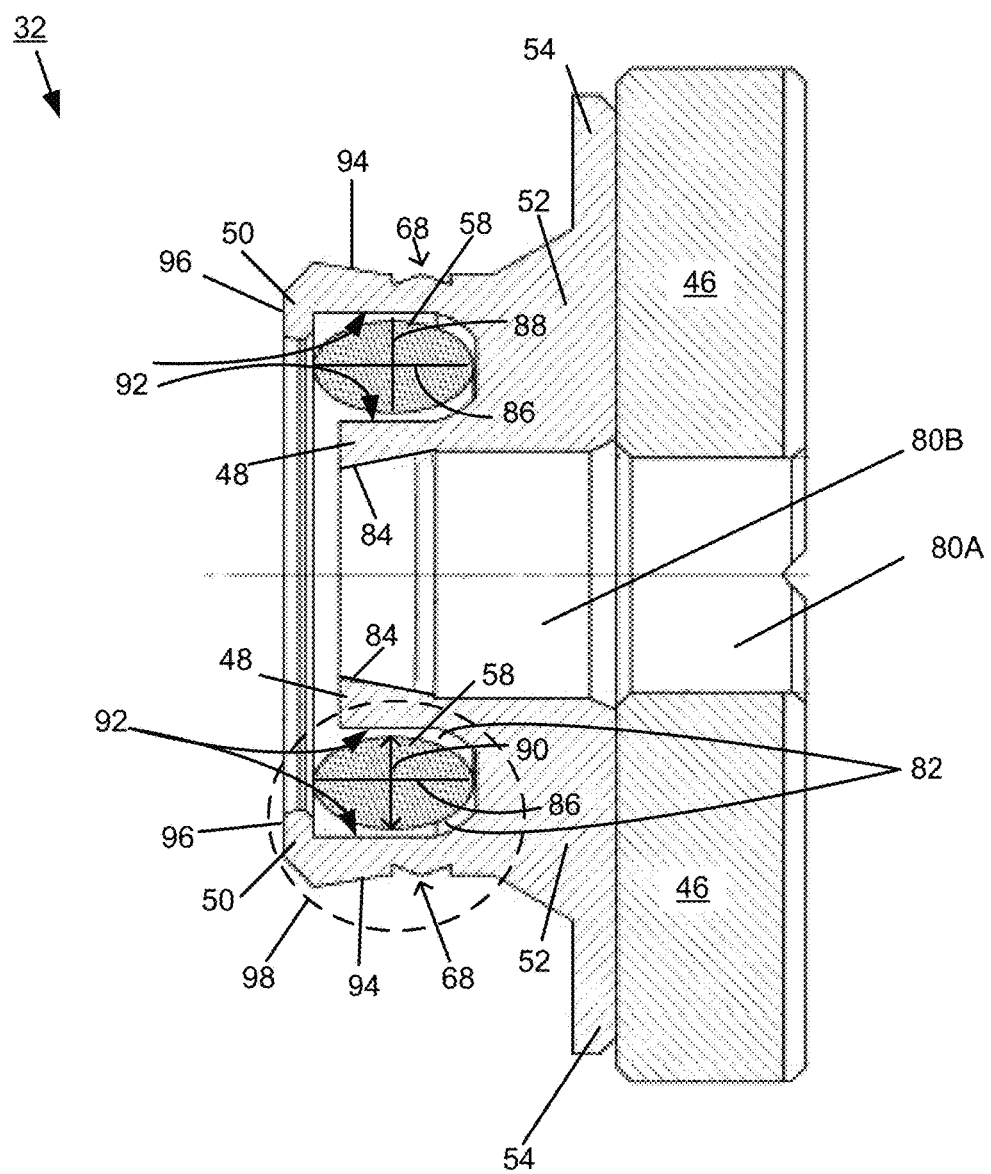
FIG. 3E is a cross-section view of the seal assembly taken along line AA in FIG. 3A.

FIG. 3E shows a cross-section view of the seal assembly in accordance with the line AA shown in FIG. 3A. The outer lip 50 has the pressure relief feature 68. The bore 80A passes axially through the backup ring 46 of the plunger seal 32; the bore 80B passes through the ring seal 44. In one embodiment, the bores 80A, 80B are approximately 0.080 inches in diameter. The inner lip 48 has a flare 84 that extends inwardly into the bore 80B, for making contact circumferentially with a surface of the plunger 30. In this embodiment, the shape of the spring 58 is represented as generally elliptical having a major axis 86 and a minor axis 88, being canted about the major axis. Within the spring pocket 56 (FIG. 4), the spring 58 is radially oriented (i.e., its major axis is generally parallel to the axis of the bore 80B) and its load line 90 approximately orthogonal to the major axis. In this orientation, the spring 58 provides a near-constant force against the interior surfaces of the inner and outer lips 48, 50.

The fluidic seals provided by the plunger seal 32 are pressure activated, the pressurized fluid (represented by arrows 92) pushing against a face of the inner lip 48, urging the flare 84 into the bore 80B and producing a seal against the surface of the plunger 30 (FIG. 2). In addition, the pressurized fluid 92 enters the spring cavity 82 and fills the spring pocket 56, pushing against the interior surface of the outer lip 50, collapsing the pressure relief feature 68 upon itself, and urging a surface portion 94 of the OD of the outer lip 50 against a gland surface of the pump head 12, thereby producing an OD seal. The collapsing of the pressure relief feature 68 upon itself reduces the contact pressure against the gland surface at the location of the relief feature, with a commensurate increase in contact pressure in neighboring regions, such as the surface portion 94. The fluidic push against the face 96 of the outer lip 50 further contributes to the forces producing this OD seal. To a lesser degree, the near-constant force provided by the spring 58 contributes to these sealing forces.

Figure 4:
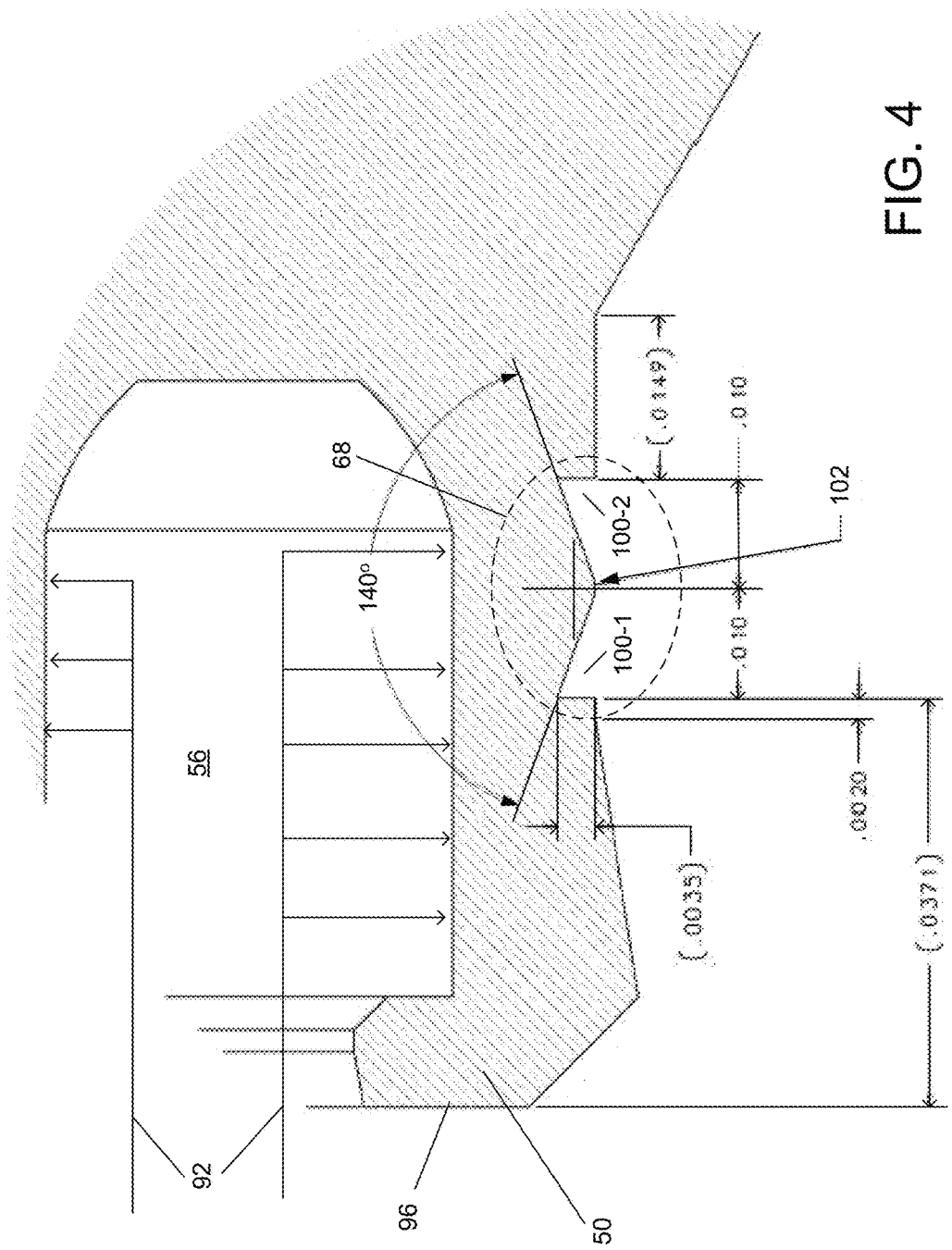
FIG. 4 is a detail view of an encircled region in FIG. 3E, the detail view showing a pressure relief feature on an outside diameter of the seal assembly of FIG. 3E.

FIG. 4 shows a detail view corresponding to a region of the seal assembly bounded by circle 98 in FIG. 3E (for simplicity purposes, without the spring 58). The bounded region includes the pressure relief feature 68. In this embodiment, the pressure relief feature 68 includes a pair of sloped grooves 100-1, 100-2 (generally 100) that converge at a ridge 102. The grooves 100 extend to a depth of approximately 0.0035 inches into the outer lip 50. Measured from the peak of the ridge 102, each groove 100 is approximately 0.010 inches in width. Groove 100-1 starts at approximately 0.371 inches from the face 96 of the outer lip 50. When collapsing upon itself, the pressure relief feature 68 deforms, being made of soft plastic, the grooves 100 almost completely disappearing as the pressurized fluid 92 urges them toward the gland surface.

Figure 5:
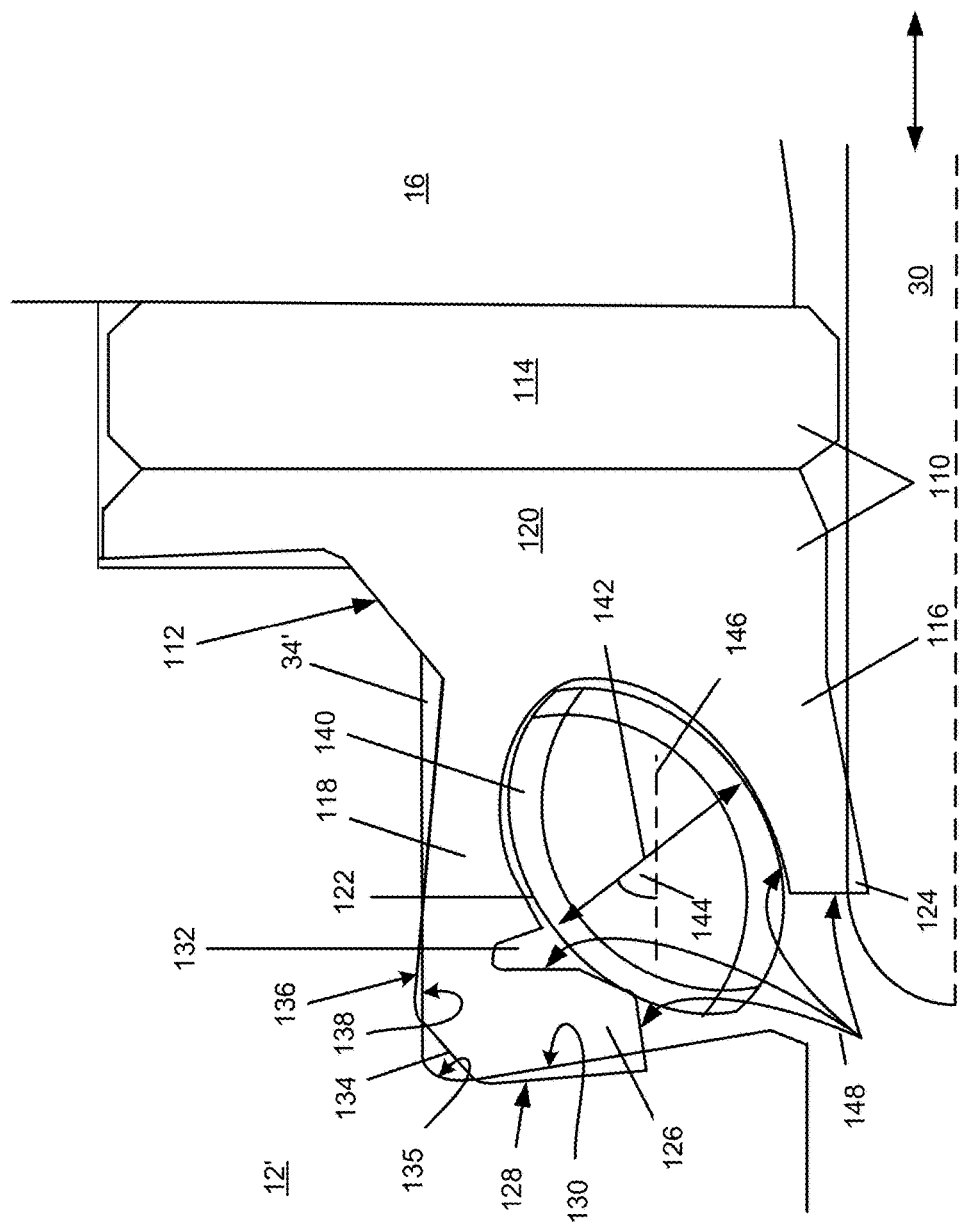
FIG. 5 is a cross-section view of a portion of another embodiment of a seal assembly having an angled spring.

FIG. 5 shows a cross-sectional view of a portion of another embodiment of a seal assembly 110. The seal assembly 110 resides within a gland 34' of a pump head 12', which is attached to the wash housing 16. (The primes (') added to the reference numerals signify that the structural elements are modified embodiments of corresponding previously described structural elements having the same reference numeral but without the prime). The seal assembly 110 includes a ring seal 112 and a backup ring 114. The ring seal 112 has an inner lip 116, an outer lip 118, and a heel portion 120, which together define a spring pocket 122. The backup ring 114 is disposed between the heel portion 120 of the seal assembly 110 and the wash housing 16.

In this embodiment, the inner lip 116 has a lip portion 124 that contacts and seals against the surface of the plunger 30. In addition, the outer lip 118 has an overhanging lip portion 126. A sealing face 128 of the lip portion 126 abuts a surface 130 of the pump head 12'. Behind the lip portion 126 is an interior notch 132, referred to herein as a pressure cavity. The outer lip 118 also has a chamfer 134. The chamfer 134 reduces some area of the lip portion 124 that comes into contact with the gland surfaces, thereby amplifying contact pressure in a vicinity of the chamfer 134, such as at the sealing face 128. In addition, the chamfer 134 facilitates installation of the seal assembly within the gland 34' A surface 136 of the OD of the outer lip 118 abuts a support surface 138 of the pump head 12'.

In the region that opposes the chamfer 134 of the lip portion 124, the gland 34' has a wedge-shaped corner 135. The sharpness of the corner 135 (which is less than 90 degrees) operates to squeeze or pinch two seal surfaces (sealing face 128, OD surface 136) of the lip portion 124 as pressurized fluid urges the chamfer 134 into the corner 135, thereby adding to the contact pressure at those surfaces.

Within the spring pocket 122 is a spring 140, arranged within the spring pocket 122 such that its load line 142 is at a predefined angle 144 configured to provide a force against an interior side of the lip portion 126 of the outer lip 118 and the lip portion 124 of the inner lip 116. This near-constant force contributes to a face seal between the sealing face 128 of the lip portion 126 and the surface 130 of the pump head 12', and to a radial seal between the lip portion 124 of the inner lip 116 and the surface of the plunger 30. Measured clockwise with respect to an axis 146, which is parallel to the axis of the plunger 30, the predefined angle 144 is preferably less than 90 degrees. This angle is only an illustrative example; any angle can be used (e.g., greater than 90 degrees), provided the load line of the spring is oriented to urge the lip portion 126 of the outer lip 118 against the surface of the pump head 12' while simultaneously urging the lip portion 124 of the inner lip 116 against the plunger surface. Preferably, the spring 144 is of the canted coil type previously described, although other types of springs can be used without departing from the principles described herein.

During actuator operation, pressurized fluid (arrows 148) fills the pressure cavity 132 and urges the sealing face 128 of the lip portion 126 more tightly against the pump head surface 12' as fluidic pressure increases. Pressurized fluid (arrow 148) also pushes against the face of the inner lip 116, to enhance the ID radial seal between the lip portion 124 and the plunger 30.

Figure 6:
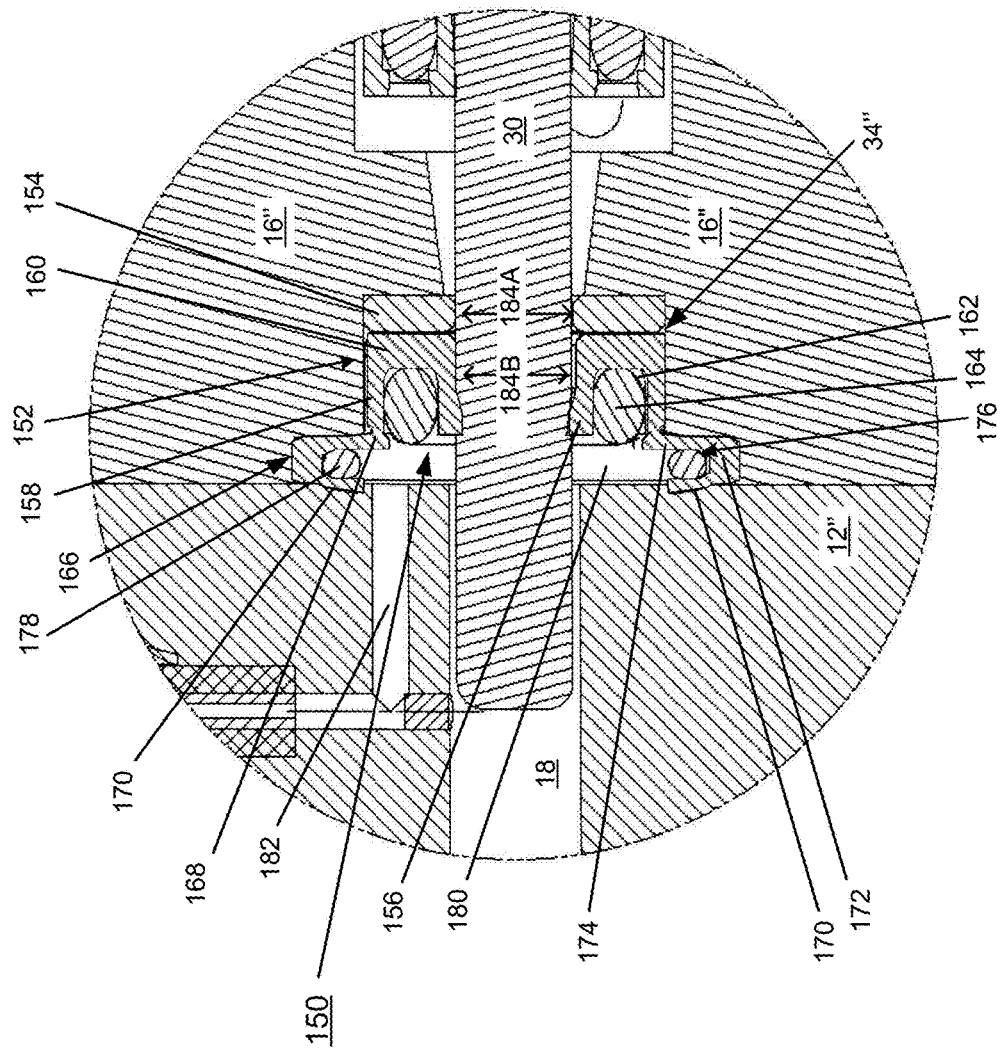
FIG. 6 is a cross-section view of an embodiment of a dual-spring seal assembly.

FIG. 6 shows a cross-sectional view of another embodiment of a seal assembly 150, referred to as a dual-spring seal assembly, for use in reciprocating and rotary plunger applications under high fluidic pressures. The dual-spring seal assembly 150 includes a ring seal 152 and a backup ring 154. In this embodiment, the seal assembly 150 resides within a gland 34" of a wash housing 16", which is attached to a pump head 12". (The double primes (") signify that the structural elements are modified embodiments of corresponding previously described structural elements having the same reference numeral but without the double prime).

Installing the seal assembly 150 within a gland 34" of the wash housing 16", instead of in the pump head 12", simplifies the process and reduces the cost of replacing the seal assembly (e.g., due to lifetime wear). In other embodiments of actuators, a gland adapted to hold the seal assembly 150 can be partially in the pump head instead of fully in the wash housing. For example, a gland of the pump head can receive a minor portion of the ring seal 152 (i.e., extension flange and OD spring), while the gland of the wash housing receives a major portion of the ring seal 152 (i.e., inner and outer lips, heel portion, and ID spring).

In addition, a gland of the pump head can be adapted to hold fully a dual-spring seal assembly, provided the shape of the seal assembly accommodates the machining of the gland in the pump head. For example, to facilitate such machining, the outer diameter of the backup ring is approximately equal to or slightly larger than the outer diameter of the ring seal (with the ring seal having a uniform outer diameter).

The ring seal 152 has an inner lip 156, an outer lip 158, and a heel portion 160; the heel portion 160 abuts the backup ring 154. The lips 156, 158 and heel portion 160 define a spring pocket 162. A first spring 164, referred to as the ID spring, is disposed within the spring pocket 162 and provides a force that urges the inner lip 156 against the plunger 30 and the outer lip 158 against the gland 34" of the wash housing 16". In one embodiment, the spring 164 is of a canted coil type that produces a near constant force. Other types of springs can be used without departing from the principles described herein.

The outer lip 158 has an extension flange 166; this extension flange 166 continues from the outer lip 158 and is connected thereto by an elbow-shaped hinge region 168. The extension flange 166 has an outer lip portion 170, a heel portion 172, and an inner lip portion 174, which together define a spring pocket 176 for holding a second spring 178, referred to as the OD spring. In one embodiment, the second spring 178 is a helical ribbon spring. Other types of springs can be used without departing from the principles described herein. The OD spring 178 provides a force that urges the outer lip portion 170 against a surface of the pump head, thereby producing a face seal, and urges the inner lip portion 174 against a gland surface of the wash housing 16".

Having the two springs 164, 178 isolates the ID sealing performance of the seal assembly from that of the OD sealing performance; the ID spring 164 contributes to the radial ID seal, while the OD spring 178 contributes to the OD face seal. The spring rate of either spring 164, 178 can be tuned without affecting the sealing performance of the other spring.

The seal assembly 150 also includes a seal cavity 180 that extends into the spring pockets 162, 176. The seal cavity 180 is in fluidic communication with an outlet channel 182 in the pump head 12". The outlet channel 182 provides a fluidic passageway by which pressurized fluid exits the pump head 12". The bore 184A passes axially through the backup ring 154; the bore 184B passes through the ring seal 152.

Figure 7C:
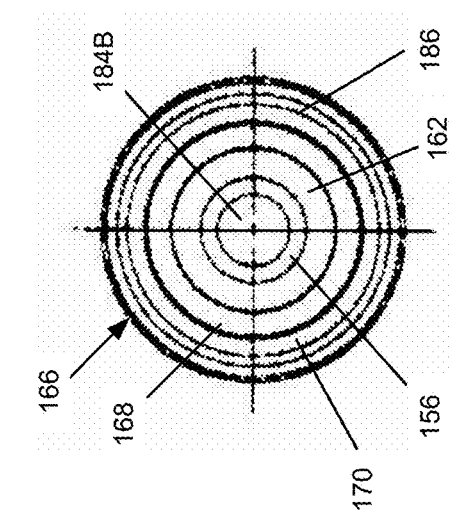
FIG. 7C is another end view of the seal assembly of FIG. 6.
Figure 7B:
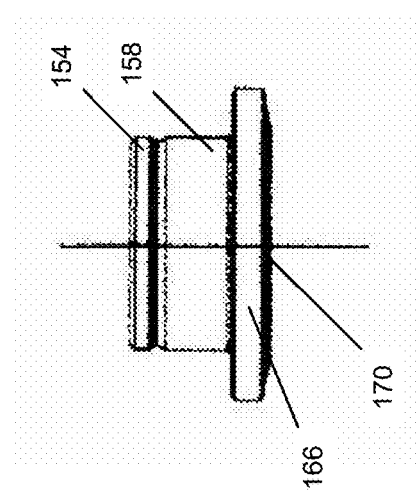
FIG. 7B is a side view of the seal assembly of FIG. 6.
Figure 7E:
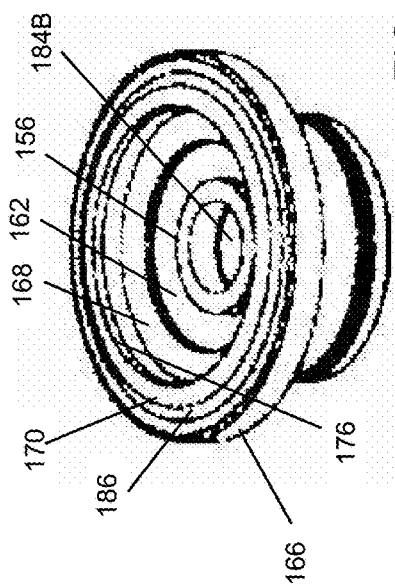
FIG. 7E is another isometric view of the seal assembly of FIG. 6 in a second orientation.
Figure 7D:
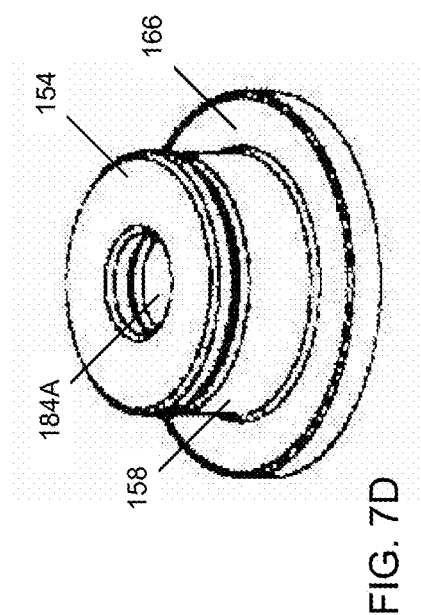
FIG. 7D is an isometric view of the seal assembly of FIG. 6 in a first orientation.
Figure 7A:
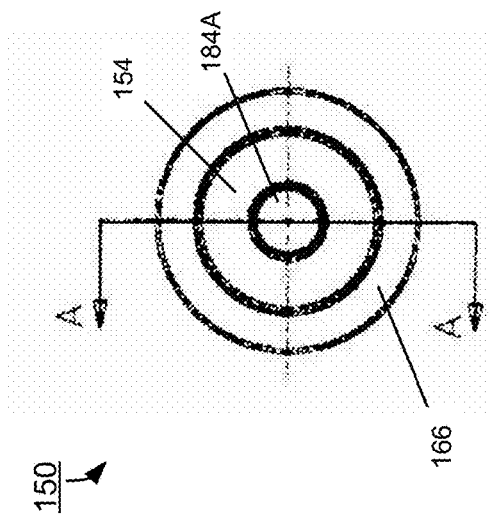
FIG. 7A is an end view of the seal assembly of FIG. 6.

FIGS. 7A-7E show various views of the seal assembly 150 of FIG. 6. FIG. 7A shows an end view of the seal assembly 150 including the extension flange 166, the backup ring 154, a central bore 184A passing through the backup ring 154, and bore 184B passing through the ring seal. The view is from the end of the seal assembly 150 that compresses into the gland 34" (FIG. 6) of the wash housing 16". Cross-section line AA passes through the center of the seal assembly 150.

FIG. 7B shows a side view of the seal assembly 150, including the backup ring 154, outer lip 158, extension flange 166, and outer lip portion 170 of the extension flange 166. FIG. 7C shows the seal assembly 150 from its other end, the ending that faces or abuts the pump head 12" when installed in the gland 34". In this end view, the various features of the seal assembly 150 appearing like concentric rings about the bore 184. Immediately surrounding the bore 184 is the inner lip 156. Around the inner lip 156 is the spring pocket 162 for holding the ID spring 164. On the other side of the spring pocket 162 is the hinge region 168 of the outer lip 158 (FIG. 7B). The next ring is the outer lip portion 170 of the extension flange 166. Where the extension flange 166 meets the outer lip portion 170 is a slight crease 186, which appears in FIG. 7C as a ring about the outer lip portion 170.

FIG. 7D shows an isometric view of the seal assembly 150, with the backup ring 154 at the top and the extension flange 166 at the bottom of the figure. FIG. 7E shows another isometric view of the seal assembly 150, here, with the extension flange 166 at the top and the backup ring 154 at the bottom of the figure.

Figure 7F:
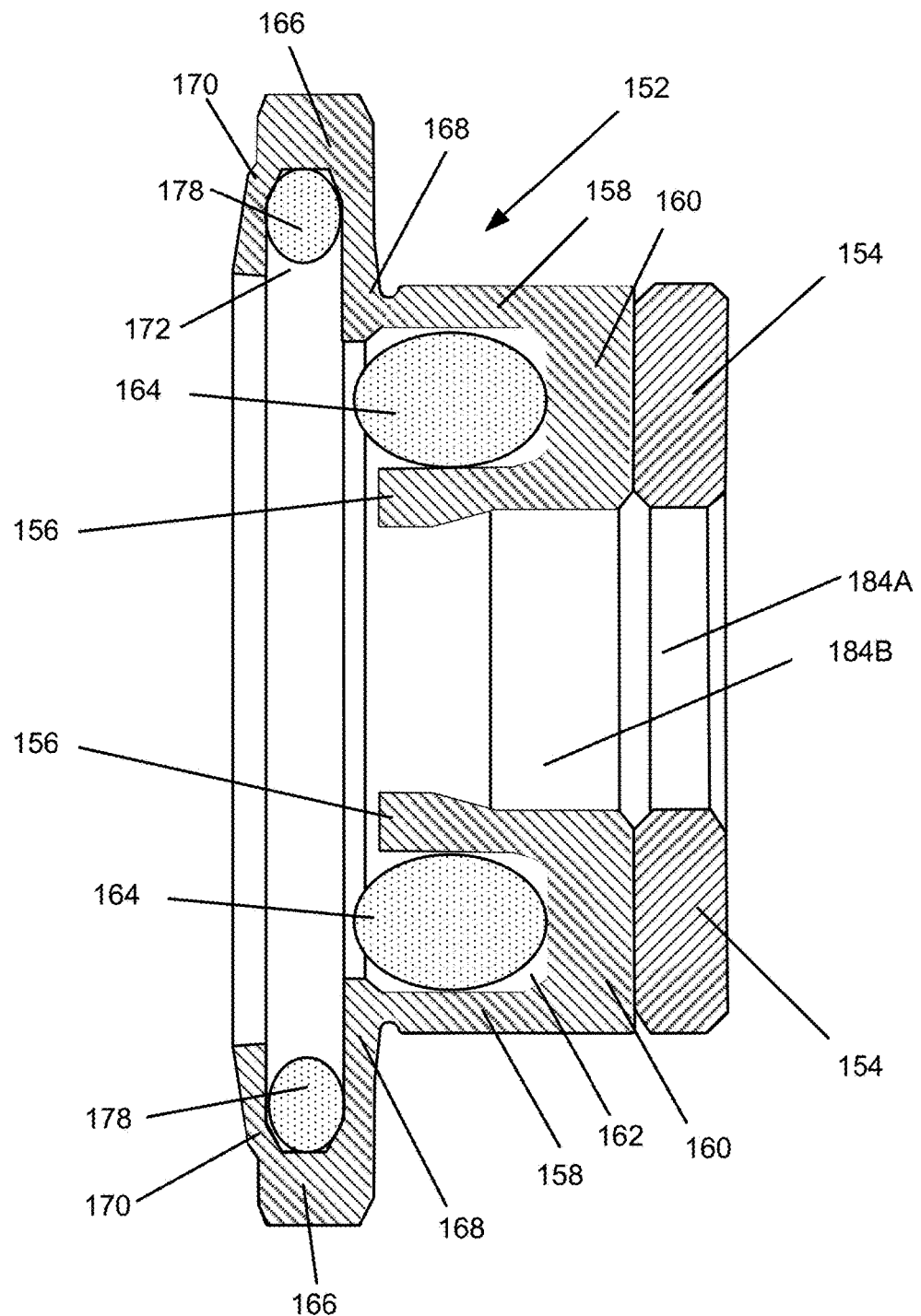
FIG. 7F is a cross-section view of the seal assembly taken along line AA in FIG. 7A.

FIG. 7F shows a cross-section view of the seal assembly 150 in accordance with the line AA shown in FIG. 7A. The bore 184B, for receiving the plunger, extends axially through the ring seal 152 and the bore 184A extends through the backup ring 154. The major heel portion 160 of the ring seal 152 abuts one side of the backup ring 154. In the spring pocket 162 defined by the inner lip 156, outer lip 158, and heel portion 160 is the ID spring 164. The hinged region 170 and extension flange 166 extend from the outer lip 158. The OD spring 178 is disposed in the spring pocket 172 behind the outer lip portion 170.

Figure 8:
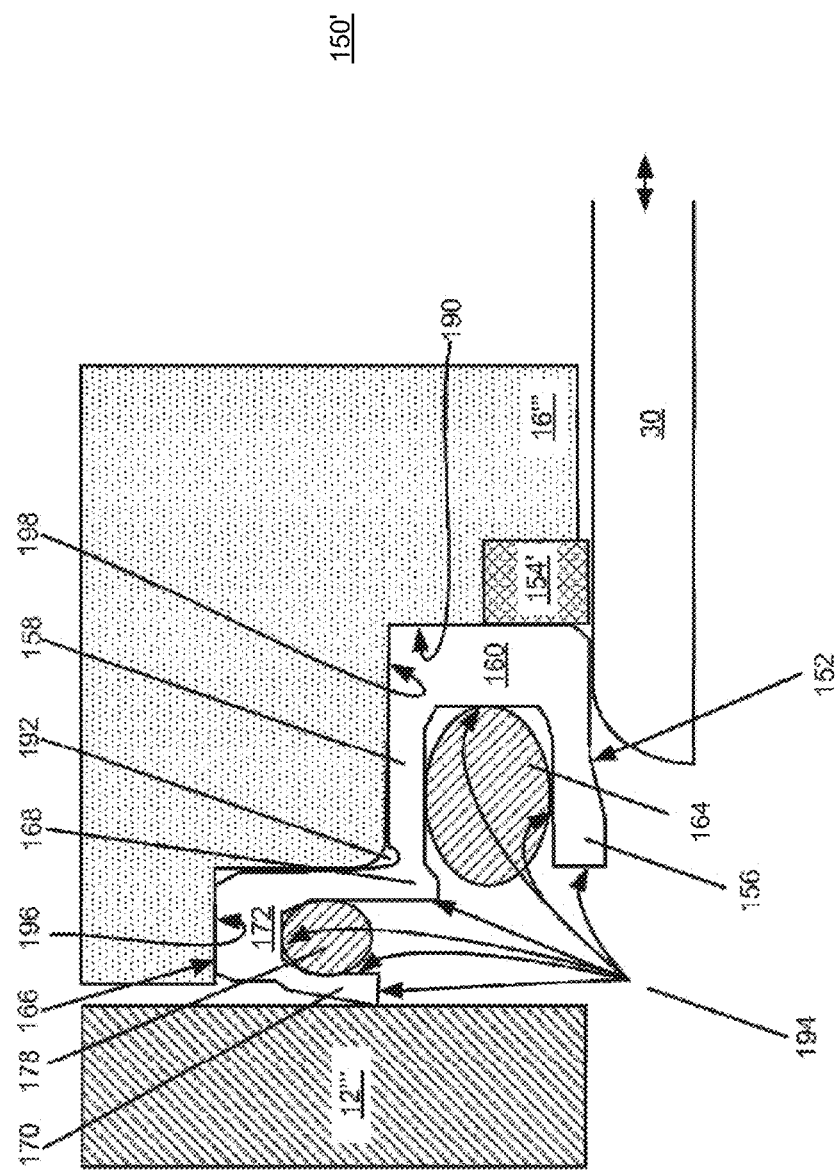
FIG. 8 is a cross-section view of a portion of another embodiment of a dual-spring seal assembly with a back-up ring that is smaller than the ring seal.

FIG. 8 shows a detail cross-sectional view of a portion of another embodiment of a seal assembly 150' similar to the seal assembly 150 shown in FIG. 6. In this embodiment, the backup ring 154' has a smaller diameter than the heel portion 160 of the ring seal 152. To accommodate the shape of the seal assembly 150', the gland 34" (FIG. 6) is modified such that some of the heel portion 160 of the ring seal 152 abuts a gland wall 190 of the wash housing 16'''. Accordingly, the effects of the manufacturing tolerances of the PEEK backup ring 154' upon the fit of the seal assembly 150' within the gland are lessened, leaving the manufacturing tolerances of the plastic ring seal 152 as the primary determinant of the tightness of fit.

The hinged portion 168 operates to take up the manufacturing tolerances of the ring seal 152. Between the hinged portion 168 and the gland surface is a gap 192. During actuator operation, pressurized fluid (represented by arrows 194) pushes against the hinge portion 168. The hinged portion 168 deforms, closing the gap 192 and abutting the gland surface. Pressurized fluid 194 also fills the spring pockets, pushing the inner lip 156 against the plunger surface to produce a radial ID seal, the outer lip portion 170 against the surface of the pump head 12''' to produce a face OD seal, the heel portion 172 of the extension flange 166 against the gland support surface 196, the outer lip 158 against the gland support surface 198, and the heel portion 160 against the gland support surface 190.

While the invention has been shown and described with reference to specific preferred embodiments, it should be understood by those skilled in the art that various changes in form and detail may be made therein without departing from the spirit and scope of the invention as defined by the following claims. For example, although described herein primarily with respect to high-pressure reciprocating applications, the various embodiments of seal assemblies can also be used in low-pressure reciprocating and rotary applications and in high-pressure rotary applications.

What is claimed is:

1. A seal assembly comprising:
    an annular body having a bore extending therethrough, the annular body having an inner lip opposed to and spaced apart from an outer lip, the inner lip having a lip portion, the outer lip having an overhanging lip portion and a notch behind the overhanging lip portion, the spaced apart inner and outer lips and the overhanging lip portion together defining a pocket, the notch extending from the pocket into the annular body; and
    a spring disposed in the pocket at an angle such that a load line of the spring is directed substantially at a pocket side of the overhanging lip portion of the outer lip and at a pocket side of the lip portion of the inner lip, the spring biasing apart the overhanging lip portion of the outer lip and the lip portion of the inner lip.

2. The seal assembly of claim 1, wherein the overhanging lip portion has a chamfer where the overhanging lip portion extends from the outer lip.

3. An actuator comprising:
    a movable rod;
    a pump head with a gland and a rod-receiving chamber;
    a wash housing abutting the pump head, the wash housing having a hole through which the movable rod extends into the chamber of the pump head; and
    a seal assembly disposed in the gland of the pump head, the seal assembly comprising:
        an annular body having a bore extending therethrough for receiving the rod, the annular body having an inner lip opposed to and spaced apart from an outer lip, the inner lip having a lip portion, the outer lip having an overhanging lip portion and a notch behind the overhanging lip portion, the spaced apart inner and outer lips and the overhanging lip portion together defining a pocket, the notch extending from the pocket into the annular body;
        a spring disposed in the pocket at an angle such that a load line of the spring is directed substantially at a pocket-side of the overhanging lip portion of the outer lip and a pocket-side of the lip portion of the inner lip, the spring biasing an exterior surface of the overhanging lip portion of the outer lip against a surface of the gland of the pump head while simultaneously biasing an exterior surface of the lip portion of the inner lip against a surface of the rod.

4. The actuator of claim 3, wherein movement of the movable rod produces pressurized fluid that fills the notch behind the overhanging lip portion, thereby urging the exterior surface of the overhanging lip portion against the surface of the gland of the pump head.

5. The actuator of claim 3, wherein the overhanging lip portion has a chamfer where the overhanging lip portion extends from the outer lip.

6. The actuator of claim 3, wherein the gland has a wedge-shaped corner opposite the chamfer of the overhanging lip portion, and wherein pressurized fluid urges the chamfer of the lip portion into the corner of the gland.

7. The actuator of claim 3, further comprising an actuator with a drive mechanism coupled to the movable rod and adapted to move the movable rod in reciprocating fashion.

8. The actuator of claim 3, further comprising an actuator with a drive mechanism coupled to the movable rod and adapted to rotate the movable rod.

9. The actuator of claim 1, wherein the notch is located on an interior of the outer lip.

10. The actuator of claim 1, wherein the notch is a pressure cavity.

11. The actuator of claim 10, wherein pressurized fluid is configured to fill the notch to urge a sealing face of the lip portion against a surface as fluidic pressure increases.

12. The actuator of claim 3, wherein the notch is located on an interior of the outer lip.

13. The actuator of claim 4, wherein the notch is a pressure cavity.

14. A seal assembly comprising:
    an annular body having a bore extending therethrough, the annular body having an inner lip opposed to and spaced apart from an outer lip, the inner lip having a lip portion, the outer lip having an overhanging lip portion and a notch behind the overhanging lip portion, the spaced apart inner and outer lips and the overhanging lip portion together defining a pocket, the notch located on an interior of the outer lip; and
    a spring disposed in the pocket at an angle such that a load line of the spring is directed substantially at a pocket side of the overhanging lip portion of the outer lip and at a pocket side of the lip portion of the inner lip, the spring biasing apart the overhanging lip portion of the outer lip and the lip portion of the inner lip.

15. The seal assembly of claim 14, wherein the notch extends from the pocket.

16. The seal assembly of claim 14, wherein the notch is a pressure cavity.

17. The actuator of claim 16, wherein pressurized fluid is configured to fill the notch to urge a sealing face of the lip portion against a surface as fluidic pressure increases.

* * * * *